United States Patent
Styrc et al.

(10) Patent No.: US 8,167,934 B2
(45) Date of Patent: May 1, 2012

(54) IMPLANT WHICH IS INTENDED TO BE PLACED IN A BLOOD VESSEL

(75) Inventors: Mikolaj Styrc, Kopstal (LU); Eric Perouse, Paris (FR)

(73) Assignee: Laboratoires Perouse, Ivry le Temple (FR)

( * ) Notice: Subject to any disclaimer, the term of this patent is extended or adjusted under 35 U.S.C. 154(b) by 670 days.

(21) Appl. No.: 11/902,900

(22) Filed: Sep. 26, 2007

(65) Prior Publication Data

US 2008/0082166 A1  Apr. 3, 2008

(30) Foreign Application Priority Data

Sep. 28, 2006  (FR) ..................................... 06 08535

(51) Int. Cl.
*A61F 2/24* (2006.01)
(52) U.S. Cl. ......................... 623/2.18; 623/2.17; 623/2.1
(58) Field of Classification Search ................. 623/2.18, 623/1.36, 1.13, 2.1, 2.17
See application file for complete search history.

(56) References Cited

U.S. PATENT DOCUMENTS

| | | | | |
|---|---|---|---|---|
| 4,044,170 | A * | 8/1977 | Scharbach et al. ............ | 427/2.27 |
| 5,824,063 | A * | 10/1998 | Cox ................ | 623/2.1 |
| 5,855,601 | A * | 1/1999 | Bessler et al. ................ | 623/2.38 |
| 5,868,783 | A * | 2/1999 | Tower ............................ | 606/198 |
| 2001/0021871 | A1* | 9/2001 | Stinson ......................... | 623/1.15 |
| 2003/0036791 | A1* | 2/2003 | Philipp et al. ................. | 623/1.11 |
| 2004/0098108 | A1* | 5/2004 | Harder et al. ................. | 623/1.15 |
| 2004/0106984 | A1* | 6/2004 | Stinson ......................... | 623/1.15 |
| 2005/0137688 | A1 | 6/2005 | Salahieh et al. | |
| 2005/0137692 | A1 | 6/2005 | Haug et al. | |
| 2005/0137693 | A1 | 6/2005 | Haug et al. | |
| 2005/0137694 | A1 | 6/2005 | Haug et al. | |
| 2005/0137695 | A1 | 6/2005 | Haug et al. | |
| 2005/0137702 | A1 | 6/2005 | Haug et al. | |
| 2007/0142906 | A1* | 6/2007 | Figulla et al. ................. | 623/2.11 |
| 2007/0282429 | A1* | 12/2007 | Hauser et al. ................. | 623/1.16 |
| 2008/0234797 | A1* | 9/2008 | Styrc ............................. | 623/1.11 |
| 2009/0062908 | A1* | 3/2009 | Bonhoeffer et al. .......... | 623/1.24 |

FOREIGN PATENT DOCUMENTS

| | | |
|---|---|---|
| EP | 1 281 375 | 2/2003 |
| FR | 2 828 263 | 2/2007 |
| WO | 03/028558 | 4/2003 |
| WO | 03/063729 | 8/2003 |
| WO | 03/063740 | 8/2003 |
| WO | 03/105695 | 12/2003 |

OTHER PUBLICATIONS

French Search Report of priority application FR 0608535.

\* cited by examiner

*Primary Examiner* — Thomas J Sweet
*Assistant Examiner* — Jason-Dennis Stewart
(74) *Attorney, Agent, or Firm* — Wenderoth, Lind & Ponack, L.L.P.

(57) ABSTRACT

This implant comprises an endoprosthesis having an axis which can be spontaneously deployed in a radial manner between a compressed configuration and a dilated configuration. The implant comprises at least one radial runner which comprises a separation surface which extends radially with respect to an outer surface of the endoprosthesis and a member which can be deployed away from the axis. The runner is arranged so as to delimit a confinement housing which extends between the separation surface and the outer surface and a radial spacer which is defined by the separation surface and the deployable member. When the implant is retained in a state of radial compression, the maximum radial width of the housing is less than the maximum radial width of the spacer which is not equal to zero.

14 Claims, 5 Drawing Sheets

IMPLANT WHICH IS INTENDED TO BE PLACED IN A BLOOD VESSEL

BACKGROUND OF THE INVENTION

I. Technical Field

The present invention relates to an implant which is intended to be placed in a blood vessel, of the type comprising:

- an endoprosthesis which has a longitudinal axis and which can be deployed spontaneously in a radial manner from a compressed configuration to a dilated configuration, the endoprosthesis delimiting an inner passage for blood flow and an outer peripheral surface;
- at least one runner for radial support which co-operates with the endoprosthesis, the runner comprising a separation surface which extends radially with respect to the outer surface and at least one member which can be deployed away from the longitudinal axis relative to the separation surface.

The invention is used in particular for the replacement of a natural cardiac valve with an endovalve.

II. Description of the Prior Art

The heart comprises valves which are present at the outlet of the right ventricle (pulmonary valve) and the left ventricle (aortic valve).

These valves provide one-way circulation of the blood flow, preventing blood reflux following the ventricular contraction.

However, illnesses can affect the valves. In particular, the valves may be subject to calcification,. which thus allows reflux or regurgitation towards the ventricle which has discharged the blood flow. The problem of regurgitation leads to abnormal dilation of the ventricle which results in cardiac insufficiency in the long term.

In order to treat this type of illness in a surgical manner, the defective valve is replaced. In this manner, it is known to implant an endovalve between the leaflets which delimit the defective valve. This endovalve is constituted by a tubular endoprosthesis which is formed by a self-expandable trellis and a flexible shutter which is produced from tissue of animal origin. The flexible shutter is permanently fixed in the endoprosthesis.

Endovalves of this type may be implanted via the endoluminal route, which considerably limits the risks associated with the implantation of the valve, in particular in terms of mortality.

In some cases, endovalves are not entirely satisfactory. After implantation of the endovalve, the leaflets of the damaged natural valve are pressed against the wall of the vessel by the outer surface of the endoprosthesis.

There is a significant risk of complications when the leaflets of the valve to be replaced extend in a region referred to as the coronary sinus, where the left and right coronary arteries open. If the coronary arteries open below the plane which extends through the free edge of the leaflets of the valve, and if the leaflets are highly calcified, the leaflets are capable of blocking the coronary arteries, which may bring about an extended infarctus, or even death of the patient.

In order to overcome this problem, it is known from FR-A-2 828 263 to provide openings in the wall of the endoprosthesis which supports the valve and to place these openings opposite the coronary arteries.

In order to ensure the axial and angular positioning of the endoprosthesis, the endoprosthesis is provided with indexing arms which engage the leaflets of the defective valve in order to abut the base of these leaflets.

After being placed in position, the endoprosthesis is deployed. The force for deploying each arm away from the endoprosthesis is significantly less than the deployment force of the endoprosthesis. The endoprosthesis therefore presses against the walls of the vessel, securing the arms and the leaflets of the valve against these walls.

A solution of this type is not entirely satisfactory when the coronary arteries open below the plane delimited by the free edge of the leaflets. In this case, the leaflets may block the coronary arteries when they are pressed against the wall of the coronary sinus when the endoprosthesis is deployed.

SUMMARY OF THE INVENTION

An object of the invention is therefore to provide an endovalve which reduces the risk of complications and mortality when it is implanted in a coronary sinus.

To this end, the present invention relates to an implant of the above-mentioned type, wherein the runner is arranged so as to delimit:

- a confinement housing which extends between the separation surface and the outer surface; and
- a radial spacer which is formed by the separation surface and the deployable member;

and wherein, when the implant is retained in a state of radial compression around the or each runner, with the endoprosthesis being in the dilated configuration thereof, the maximum radial width of the housing is less than the maximum radial width of the spacer, the spacer having a maximum radial width which is not equal to zero.

The implant according to the invention may comprise one or more of the following features, taken in isolation or according to any technically possible combination:

- the force for deploying the deployable member away from the separation surface is greater than the total of the radial deployment force of the endoprosthesis and the force for retaining the separation surface in a remote state relative to the outer surface, when the implant is retained in a state of radial compression around the or each runner;
- the or each runner is permanently mounted on the endoprosthesis;
- the or each runner is integral with the endoprosthesis;
- the endoprosthesis comprises a trellis which is formed by at least one resilient filament, the or each runner being formed by an extension of at least one filament of the trellis;
- an edge of the separation surface is articulated to an edge of the outer surface;
- the or each runner is mounted in a detachable manner on the endoprosthesis;
- the or each runner comprises a rigid tubular support which is pressed on the outer surface during operation, the spacing member being able to be deployed radially from the tubular support;
- the deployable member is articulated to the separation surface;
- the or each runner has a cross-section, taken in a center plane which extends through the longitudinal axis, substantially in the form of a V;
- the endoprosthesis comprises a shutter which is permanently mounted in the inner passage, the shutter having a cross-section, taken in a centre plane which extends through the longitudinal axis, which converges in the opposite direction to the V-shaped cross-section of the or each runner;
- the spacer is permeable with respect to liquids.

BRIEF DESCRIPTION OF THE DRAWINGS

The invention will be better understood from a reading of the following description, given purely by way of example and with reference to the appended drawings, in which.

DESCRIPTION OF THE INVENTION

Figure 1:
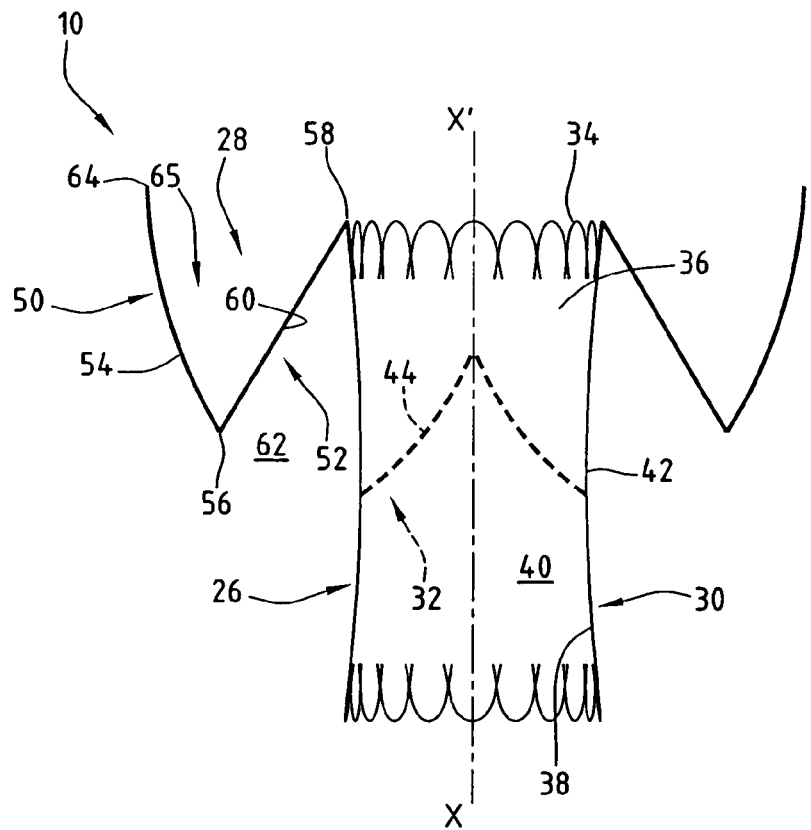
FIG. 1 is a section along an axial centre plane of a first implant according to the invention in a completely deployed state.

A first implant 10 according to the invention is illustrated in FIGS. 1 to 4. This implant 10 is intended to replace a defective natural valve 12 which can be seen in FIG. 3, in the coronary sinus 14.

The natural valve 12 comprises leaflets 16 which have a lower edge 17 which is articulated in the lower portion of the coronary sinus 12 and a free upper edge 18.

The coronary sinus 14 is delimited by a flared wall 20. Two coronary arteries 22, one of which can be seen in FIG. 3, open in the wall 20 through an opening 24.

In this example, the opening 24 is located opposite the leaflets 16 when these are pressed against the wall 20. It is therefore capable of being blocked by the leaflets 16.

Figure 2:
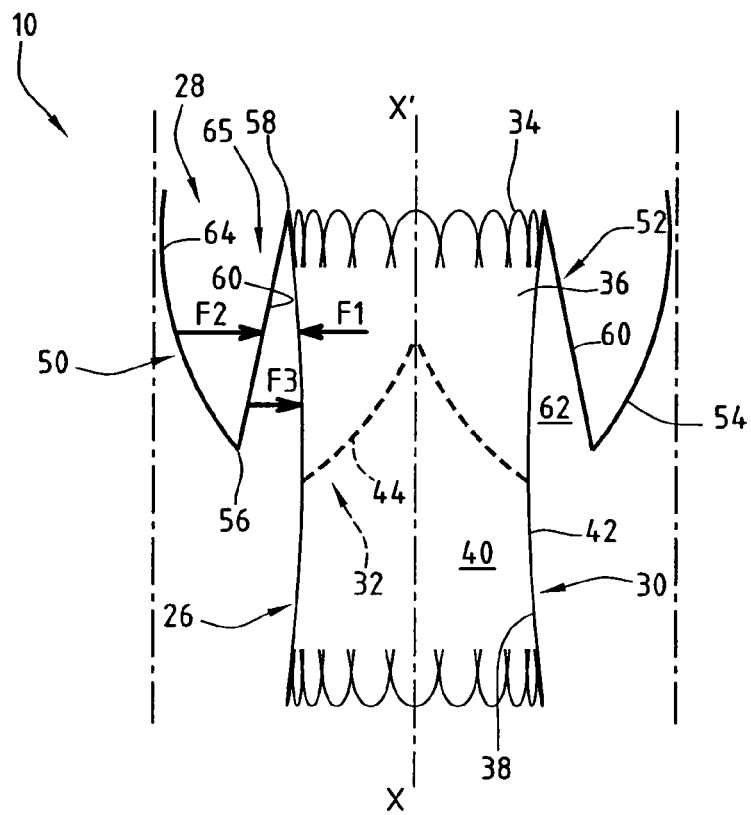
FIG. 2 is a view similar to FIG. 1 in a partially radially contracted state.

As illustrated by FIGS. 1 and 2, the implant 10 comprises an endovalve 26 having a longitudinal axis X-X', and the runners 28 which are permanently mounted on the endovalve protruding radially away from the axis X-X' of the endovalve 26.

The endovalve 26 comprises a tubular endoprosthesis 30 and a shutter 32 which is permanently fixed in the endoprosthesis 30.

The endoprosthesis 30 is formed, for example, by a tubular trellis 34 having interwoven filaments, embedded in an extendable film 36 which is liquid-tight, such as an elastomer material.

The trellis 34 is constituted by stainless steel which has resilient properties, so that the endoprosthesis 30 is self-expandable. An endoprosthesis of this type, when it is used alone, is generally referred to as a "stent". In a variant, the trellis 34 is formed on the basis of shape-memory metal or a flexible polymer fibre.

As known per se, the endoprosthesis 30 is capable of changing shape spontaneously from a compressed configuration, in which it has a small diameter, to a dilated configuration, in which it has a greater diameter, this dilated state constituting the rest state thereof. A radial force $F_1$ for deployment of the endoprosthesis is therefore generated when the endoprosthesis 30 occupies an intermediate configuration between the compressed configuration and the dilated configuration.

The endoprosthesis 30 defines, around the axis X-X' an inner surface 38 which delimits a central passage 40 for circulation of the blood and an outer surface 42 which is substantially cylindrical and which is intended to be partially pressed against a wall 20 of a blood vessel, as will be seen below.

In conventional manner, the shutter 32 is formed by flexible membranes 44 which are fixed in a central portion of the separation surface 38.

Each membrane 44 is formed by a film of polymer or a layer of organic film such as calf pericardium. It generally has a rectangular shape. Each membrane 44 is connected to the inner surface 38 of the sealed film 36 along a large side which forms a base along the connection circumference of this surface 38.

As known per se, the longitudinal edges of the membranes 44 are connected to the tubular endoprosthesis 30 along three generating lines thereof which are regularly distributed in an angular manner around the axis of the tubular endoprosthesis. In this manner, the membranes 44 are connected in pairs along the longitudinal edges thereof to the endoprosthesis 30.

The membranes 44 can be deformed between a blocking position illustrated in FIG. 1 in which the free edges of the membranes 44 are joined in pairs through the middle, and a position for passage of the blood flow in which the membranes 44 are mutually spaced-apart.

In the blocking position, the three membranes 44 form a shutter having a V-shaped cross-section which opens downwards in a centre plane which extends through the axis X-X'.

Figure 3:
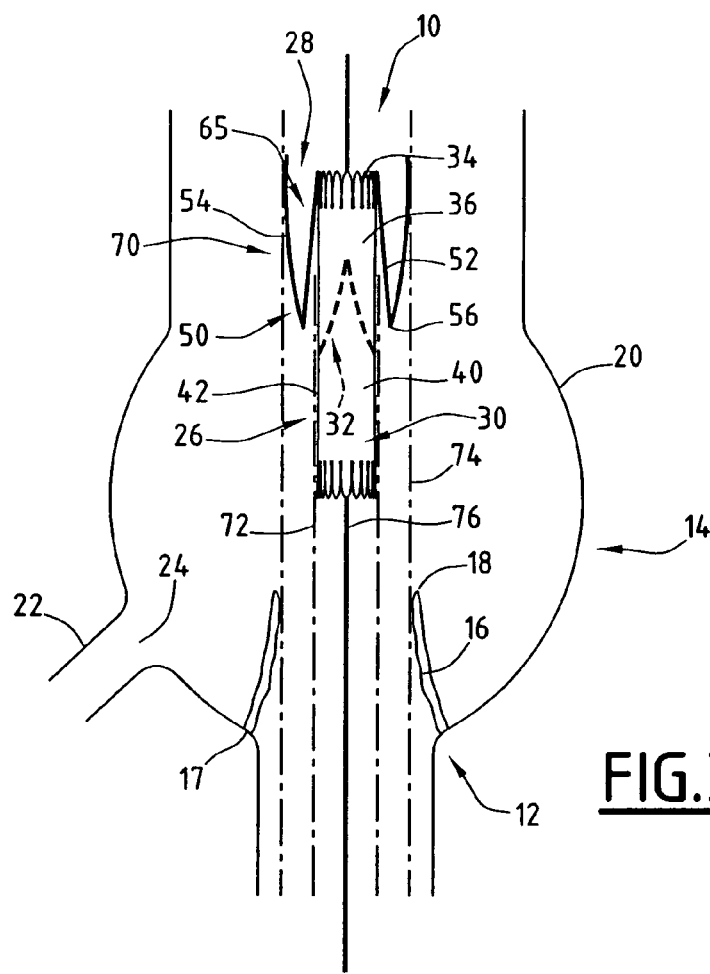
FIG. 3 is a schematic section of a coronary sinus in which the implant of FIG. 1 will be arranged and retained in a completely retracted state.

In the example illustrated in FIGS. 1 to 3, the runners 28 are formed by deployable arms 50 which protrude radially away from the axis X-X', starting from and facing the outer surface 42. In this example, the implant 10 comprises at least two arms 50 which are arranged at one side and the other of a center plane which extends through the axis X-X' of the endoprosthesis 30. The arms 50 are integral with the filaments which constitute the trellis 34. They are thus formed, for example, by loops which extend filaments of the trellis 34.

Each arm 50 has a V-shaped vertical cross-section which opens upwards, taken along an axial center plane.

Each arm 50 comprises a portion 52 for connection to the endoprosthesis 30 and a spacing portion 54, the portions 52, 54 defining an elbow-like member 56 which is directed downwards.

The connection portion 52 extends downwards from the upper edge of the outer surface 42 as far as the elbow-like member 56 which is located opposite a central portion of the outer surface 42. The connection portion 52 defines a separation surface 60 which is located opposite the outer surface 42 of the endoprosthesis 30. The separation surface 60 defines with the outer surface 42 an intermediate housing 62 for confinement of a leaflet 16.

The connection portion 52 can be moved spontaneously relative to the outer surface 42 from a contracted position in which the separation surface 60 is pressed against the outer surface 42 to a radially expanded position which constitutes the rest state thereof and in which the separation surface 60 is located radially remote from the outer surface 42.

In the expanded position, the connection portion 52 forms an angle of between 10° and 60° with the outer surface 42, taken in the region of the upper edge. A radial force $F_3$ for retaining the separation surface 60 with spacing from the outer surface 42 is generated when the connection portion 52 occupies an intermediate position between the contracted position and the expanded position thereof.

The spacing portion 54 extends upwards and away from the axis X-X' between the elbow-like member 56 and a free end 64 which is intended to be pressed against a wall 20 of a blood vessel.

The free end 64 is folded in the form of a loop in order to prevent the wall on which it is pressed from becoming perforated.

The spacing portion 54 has substantially the same length as the connection portion 52. In this manner, the free end 64 is substantially located in the same plane as the upper edge 58 of the surface 42.

The spacing portion 54 can be moved spontaneously from a retracted position, in which it is placed against the separation surface 60 of the connection portion, to a deployed position in which it extends radially away from the surface 60. In this deployed position, the spacing portion 54 forms, with the connection portion 52, an angle of between 20° and 60°.

The spacing portion 54 forms with the connection portion 52 a radial spacer 65 which is permeable with respect to liquids and which is intended to retain a portion of the outer surface 42 of the endoprosthesis 30 and the leaflets 16 of the natural valve in a state remote from the wall 20.

When the spacing portion 54 occupies an intermediate position between the retracted position thereof and the deployed position thereof, a radial force $F_2$ for deploying the spacing portion 54 away from the separation surface 60 is generated.

As illustrated in FIG. 2, the force $F_2$ for deploying the spacing portion 54 away from the separation surface 60 is greater than the total of the force $F_3$ for retaining the separation surface 60 with spacing relative to the outer surface 42 and the force $F_1$ for radial deployment of the endoprosthesis 30 from the contracted configuration to the dilated configuration thereof, when the implant 10 is retained in a state of radial compression around each runner 28, for example, in a tube which is located outside the human body.

In this configuration, the maximum radial width of the housing 62, taken between the outer surface 42 and the separation surface 60, is less than the maximum radial width of the spacer 65, taken between the spacing portion 54 and the separation surface 60 of the connection portion. The spacer 65 further has a maximum radial width which is not equal to zero.

Figure 4:
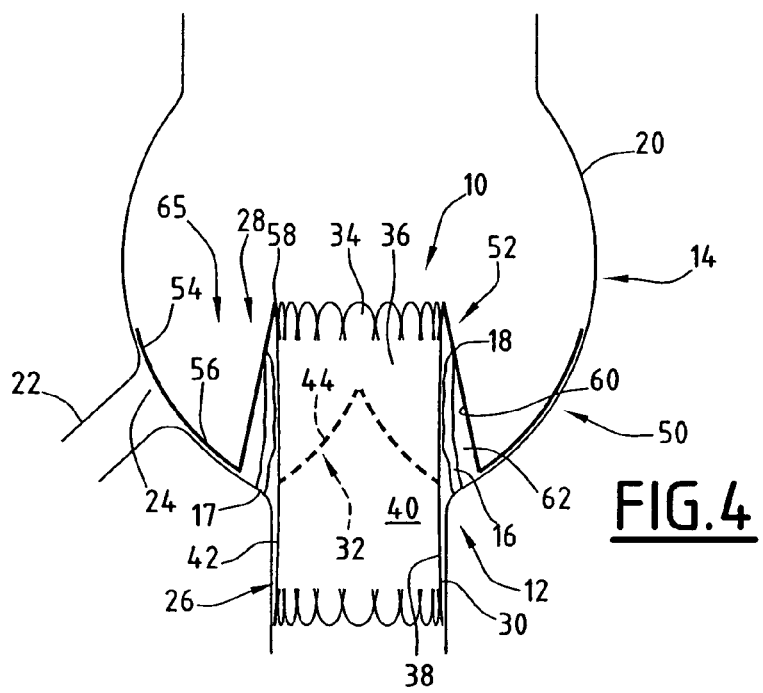
FIG. 4 is a view similar to FIG. 3, the implant having been implanted.

The method for implanting the implant 10 in the coronary sinus 12 will now be described with reference to FIGS. 3 and 4.

Initially, the implant 10 is loaded in a deployment device 70 comprising means 72, 74 for selective deployment of the runners 28 and the endoprosthesis 30.

In this example, the deployment device 70 is formed by an inner sheath 72 which retains the endoprosthesis 30 in the contracted configuration thereof, and an outer sheath 74 which retains the runners 28 in a retracted state.

The inner sheath 72 extends around the outer surface 42 of the endoprosthesis 30. It has an upper end which is inserted between the endoprosthesis 30 and the separation surface 60 of the runners 28.

The outer sheath 74 is mounted in a coaxial manner with the sheath 72 around the runners 28. It retains the connection portion 52 in its contracted position against the endoprosthesis 30 and the spacing portion 54 in its retracted position against the connection portion 52.

Then, a surgical guide 76 is introduced, via the endoluminal route, as far as the coronary sinus 14. The deployment device 70 in which the implant 10 has been loaded is moved into the coronary sinus 14 by sliding the endoprosthesis 30 around the guide 76. The implant 10 is placed above the leaflets 16 of the natural valve 12.

The outer sheath 74 is then withdrawn by means of sliding along the inner sheath 72. During this withdrawal, the runners 28 are deployed. To this end, the connection portion 52 moves away from the outer surface 42 under the action of the force $F_3$. In the same manner, the spacing portion 54 is deployed away from the separation surface 60 of the connection portion under the effect of the force $F_2$.

Then, the implant 10 and the inner sheath 72 are moved downwards in order to introduce the leaflets 16 of the natural valve 12 into the housings 62 which are located between the outer surface 42 of the endoprosthesis 30 and the separation surface 60 of the runners 28.

During this movement, the spacing portions 54 of the arms 50 are pressed against the wall 20 of the coronary sinus 14. The implant 10 is then secured in position in the sinus 14.

Then, the inner sheath 72 is withdrawn in order to remove the endoprosthesis 30 from the sheath 72.

During this withdrawal, the endoprosthesis 30 is deployed radially away from the axis X-X' thereof. However, since the total of the force $F_1$ for radial deployment of the endoprosthesis 30, and the force $F_3$ for retaining the separation surface 60 with spacing relative to the outer surface 42 is less than the force $F_2$ for deployment of the spacing portion 54, the spacing portion 54 remains remote from the connection portion 52. The angle formed between the portions 52, 54 remains greater than at least 10°.

In this manner, the upper portion of the outer surface 42 of the endoprosthesis 30 located opposite the runners 28 is retained with spacing from the wall 20 and therefore the openings 24 when the lower portion of the surface 42 located below the runners 28 is pressed on the wall 20.

The leaflets 16 are confined in the housings 62, which eliminates the risk of the coronary arteries 22 becoming blocked. A coronary perfusion is therefore permanently maintained through the spacers 65, even after deployment of the endoprosthesis.

A method has therefore been described for deployment of an implant 10 which is intended to be placed in a blood vessel 14, the implant being of the type comprising:

an endoprosthesis 30 having a longitudinal axis X-X' which can be deployed spontaneously in a radial manner between a compressed configuration and a dilated configuration, the endoprosthesis 30 delimiting an inner passage 40 for blood flow and an outer peripheral surface 42;

at least one radial runner 28 which co-operates with the endoprosthesis 30, the runner 28 comprising a separation surface 60 which extends radially with respect to the outer surface 42 and at least one spacing member 54 which can be deployed away from the longitudinal axis X-X' relative to the separation surface 60.

In this method, the spacing member 54 of each runner 28 is retained with radial spacing from the separation surface 60 and the outer surface 42, after deploying the endoprosthesis 30 into the dilated configuration thereof in the vessel 14.

A portion of the outer surface 42 of the endoprosthesis 30 in the dilated configuration thereof is thus retained with radial spacing from the wall 20 of the vessel 14, in particular opposite the openings 24 in which the coronary arteries 22 open.

In a variant, the runner 28 is peripheral. The portions 52 and 54 form skirts which extend in a peripheral manner around the axis X-X'.

Figure 5:
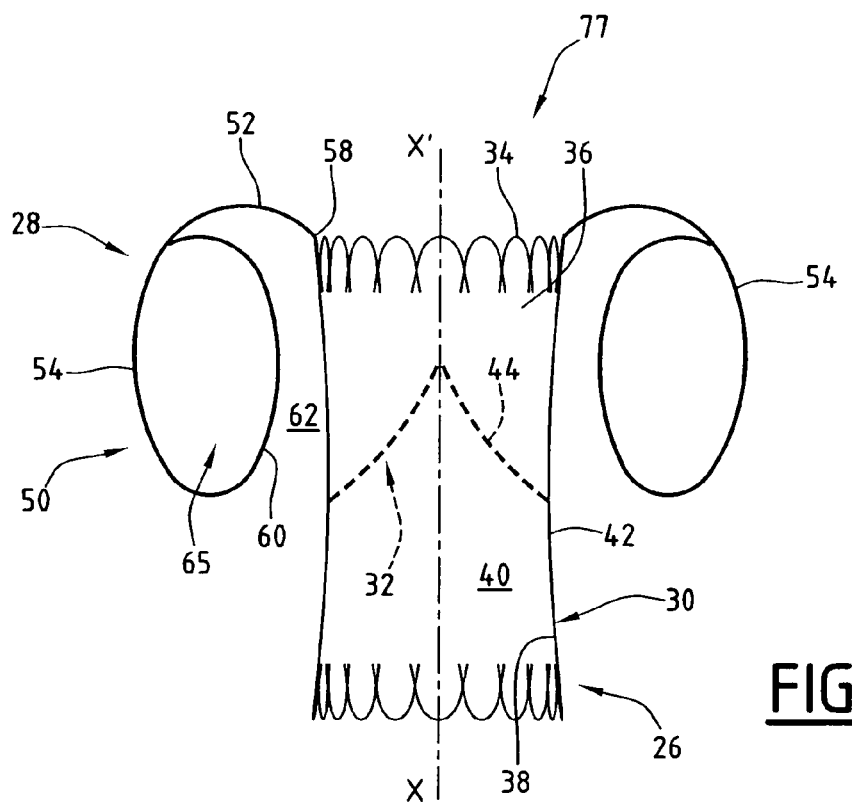
FIG. 5 is a view similar to FIG. 1 of a second implant according to the invention.

A second implant 77 according to the invention is illustrated in FIG. 5. The second implant 77 differs from the first implant 10 in that the runners 28 comprise a spacer 65 in the form of a closed loop, in a vertical cross-section taken along an axial plane extending through the axis X-X' of the endoprosthesis 30.

The spacer 65 and the connection portion 52 are integral. The portion 52 further extends substantially horizontally from the upper edge of the surface 42.

In this example, the spacer 65 defines a separation surface 60 which is located opposite the outer surface of the endoprosthesis 42, and a support surface which is located radially with respect to the separation surface.

The operation of this implant 77 is similar to that of the first implant 10. When the implant 77 is retained in a state of radial compression around the runners 28, the maximum radial width of the housing 62 is less than the maximum radial width of the spacer 65.

Figure 6:
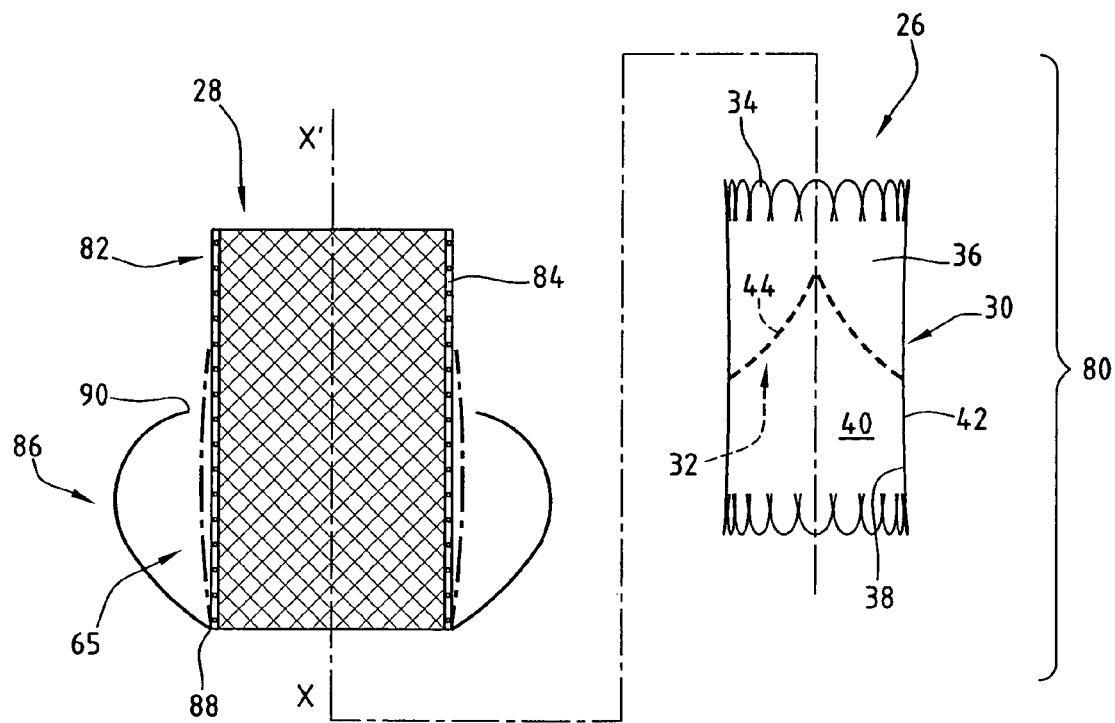
FIG. 6 is a view similar to FIG. 1 of a third implant according to the invention.

A third implant 80 according to the invention is described in FIG. 6. In this example, the endovalve 26 is formed by a tubular endoprosthesis 30 which is provided with a shutter 32 as described above.

In contrast to the implant 10 illustrated in FIGS. 1 to 5, the runner 28 is not permanently mounted on the endovalve 26. The runner 28 is formed by a tubular support 82 which can be removed with respect to the endovalve 26.

The support 82 comprises a tubular trellis 84 which comprises a reinforcement of filaments embedded in a polymer film and at least two flexible spacing members 86 which are placed at one side and the other of a centre plane which extends through the axis X-X' of the support 82.

The trellis 84 can be deployed spontaneously in a radial manner between a compressed configuration and a dilated configuration which constitutes the rest configuration thereof.

Each member 86 comprises a lower end 88 which is fixedly joined to the lower edge of the support 82 and a free end 90 which is placed opposite the trellis 84 of the support 82.

The axial flexibility of the members 86 is greater than that of the trellis 84.

As illustrated in FIG. 6, the members 86 can be moved spontaneously between a retracted upper position which is illustrated with dot-dash lines in FIG. 6, and a radially deployed lower position which is illustrated with dotted lines in FIG. 6.

In the retracted position, each member 86 is held substantially pressed against an outer surface of the trellis 84 along a generating line of the trellis 84. The free end 90 is placed opposite an upper point of the trellis 84. The member 86 is I-shaped.

In the deployed position, which constitutes a rest position, the free end 90 has moved downwards and is located below the upper point opposite the trellis 84. The distance which separates the free end 90 from the lower end 88 is reduced, and the member is C-shaped. It protrudes away from the outer surface of the trellis 84.

The spacer 65 is thus formed by the trellis 84 and the members 86. The housing 62 for confinement of the leaflets 16 of the natural valve 12 is defined between the outer surface 42 of the endoprosthesis 30 and an inner surface of the trellis 84.

Figure 7:
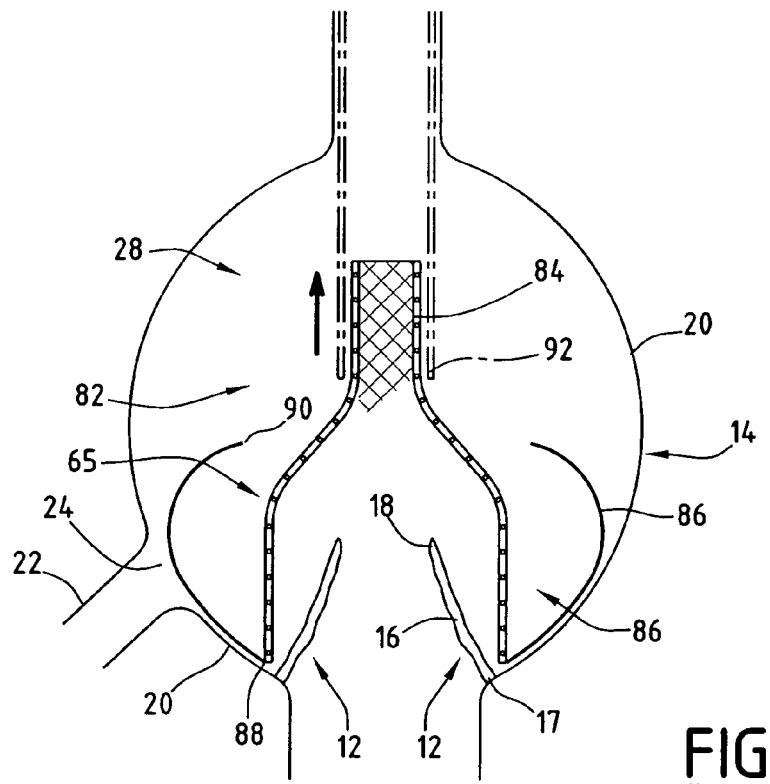
FIG. 7 is a view similar to FIG. 3 during a first step for implantation of the third implant.
Figure 8:
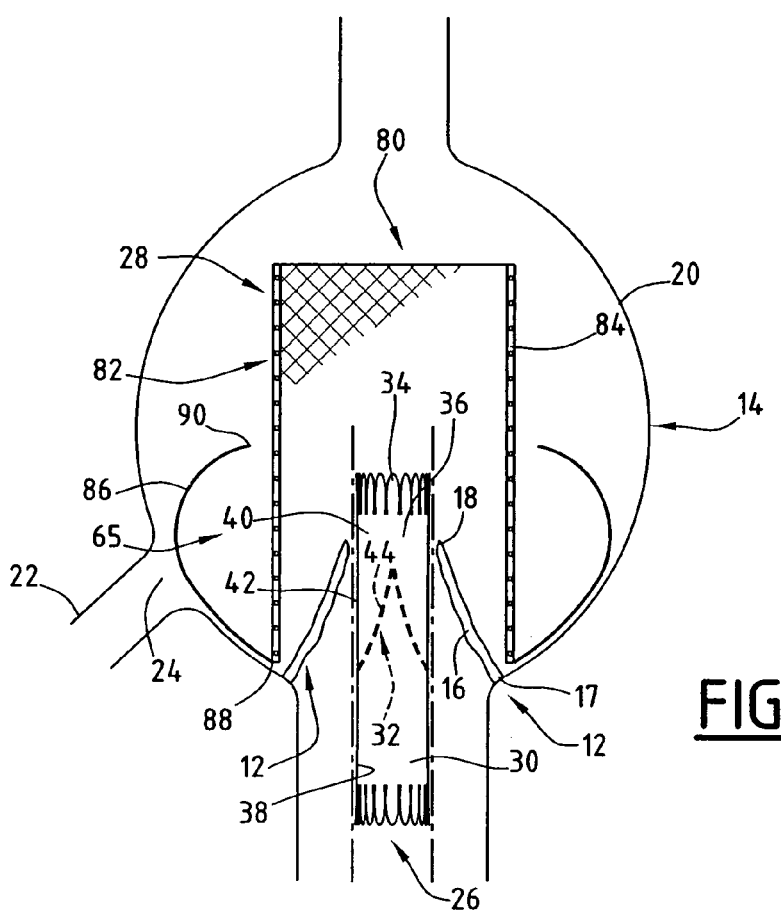
FIG. 8 is a view similar to FIG. 7 during a second step for implantation of the third implant.
Figure 9:
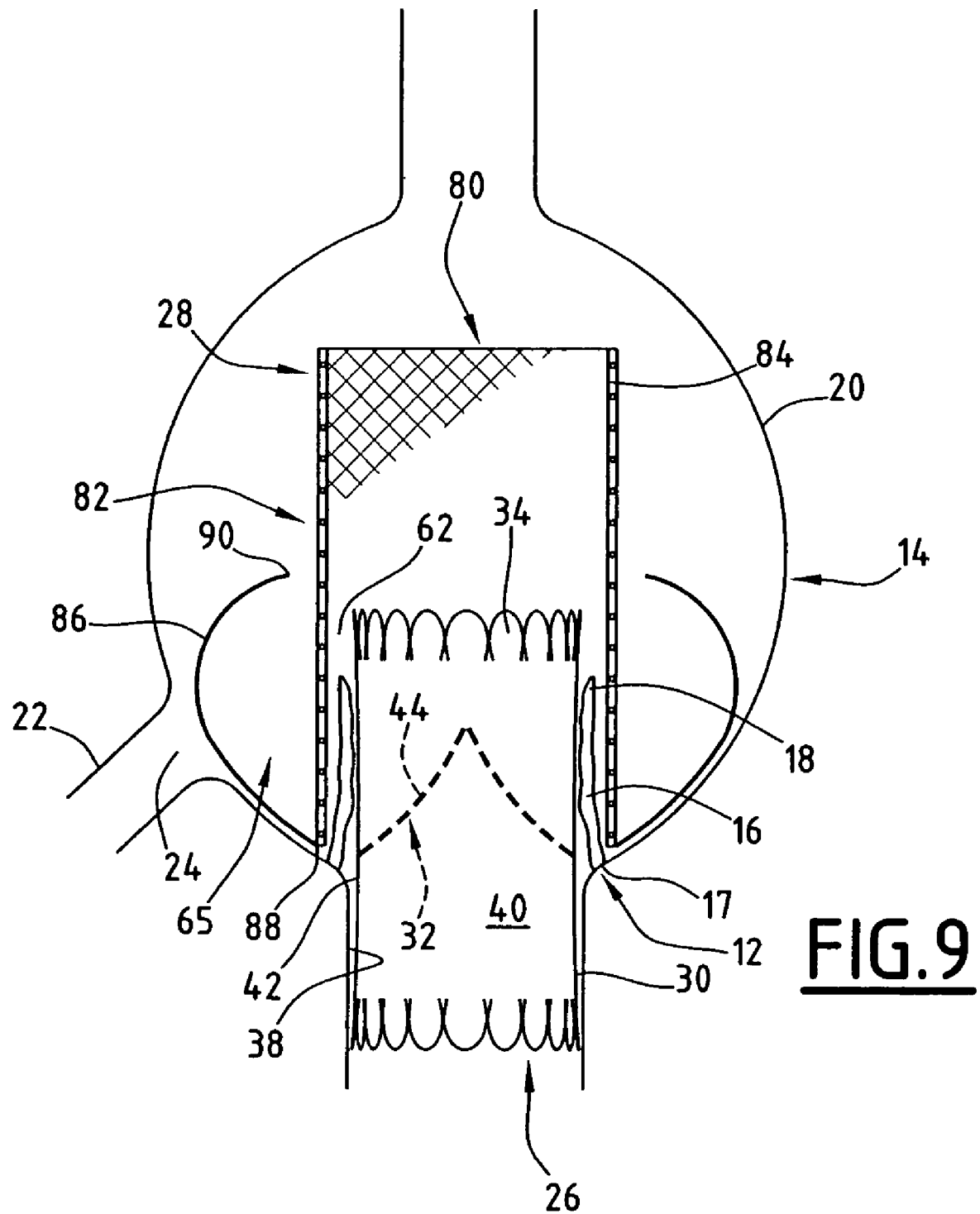
FIG. 9 is a view similar to FIG. 7 during a third step for implantation of the third implant.

The method for implanting the second implant 80 in the coronary sinus 14 will now be described with reference to FIGS. 7 to 9.

Initially, the runner 28 is loaded in a deployment device comprising an outer sheath (not illustrated) for retaining the members 86 in their retracted position and an inner sheath 92 for retaining the tubular support in the retracted configuration thereof. The inner sheath 92 is interposed between the members 86 and the outer surface of the trellis 84. The runner 28 is thus brought into the coronary sinus 14 in order to be deployed around the natural valve 12.

The runner 28 is placed above the natural valve 12. The outer sheath is withdrawn by means of sliding in order to bring about the radial deployment of the members 86 towards the deployed position thereof. Then, the inner sheath 92 is partially withdrawn in order to bring about the radial deployment of the lower end of the trellis 84, as illustrated in FIG. 7.

The runner 28 is moved towards the valve 12. The leaflets 16 of the natural valve 12 are engaged inside the trellis 84 and the lower edge of the trellis 84 presses against the wall 20 around the natural valve 12. The spacing members 86 are pressed against the wall 20 of the sinus 14 as illustrated in FIG. 8.

The trellis 84 is then totally removed from the inner sheath. It is in the dilated configuration thereof. The outer surface of the trellis 84 is retained with spacing from the wall 20 opposite the openings 24 by means of the members 86.

Then, the endovalve 26 is brought into the compressed configuration thereof in the coronary sinus 14 inside the tubular support 82. The endovalve 26 is engaged through the natural valve 12. The leaflets 16 are placed between the endovalve 26 and the tubular support 82.

The endovalve 26 is then deployed to the dilated configuration thereof. During this deployment, the outer surface 42 of the endoprosthesis 30 is pressed against an inner surface of the trellis 84, the leaflets 16 being secured. In this manner, these leaflets 16 are retained in the housing 62 delimited between the inner surface of the support 82 and the outer surface 42 of the endovalve 26.

The force for deploying the members 86 away from the trellis 84 is greater than the total of the force which is substantially equal to zero for retaining the trellis 84 with spacing relative to the outer surface 42 of the endoprosthesis 30 and the force for radial deployment of the endoprosthesis 30. In this configuration, the maximum radial width of the housing 62 is less than the maximum radial width of the spacer 65.

A coronary perfusion is therefore provided at all times by the spacing members 86 which prevent the trellis 84 from being pressed against the wall 20 of the coronary sinus 14 with respect to each coronary artery 22. In this manner, the risk of complications during the implantation of the endovalve 26 is reduced.

The invention claimed is:

1. An implant for placement in a blood vessel, the implant comprising:
   an endoprosthesis having a longitudinal axis, and being configured to generate a radial deployment force so as to be deployed spontaneously in a radial manner from a compressed configuration to a dilated configuration, the endoprosthesis delimiting an inner passage for blood flow and an outer peripheral surface;
   at least one runner for radial support and co-operating with the endoprosthesis, the at least one runner comprising a separation surface extending radially with respect to the outer peripheral surface and at least one member being configured to be deployed away from the longitudinal axis relative to the separation surface;
   wherein the runner is arranged so as to delimit a confinement housing which extends between the separation surface and the outer peripheral surface; and
   a radial spacer which is formed by the separation surface and the at least one member, and is configured to generate a force to deploy the at least one member away from the separation surface;

wherein, when the implant is retained in a state of radial compression around the at least one runner, with the endoprosthesis being in the dilated configuration, the maximum radial width of the confinement housing is less than the maximum radial width of the spacer, the spacer having a maximum radial width which is not equal to zero;

wherein the runner is configured to generate a radial force so as to deploy the radial spacer away from the separation surface; and wherein the force generated by the radial spacer for deploying the at least one member away from the separation surface is greater than the total of the radial deployment force generated by the endoprosthesis and the force for retaining the separation surface in a remote state relative to the outer peripheral surface, when the implant is retained in a state of radial compression around the at least one runner.

2. An implant according to claim 1, wherein the at least one runner is permanently mounted on the endoprosthesis.

3. An implant according to claim 2, wherein the at least one runner is integral with the endoprosthesis.

4. An implant according to claim 3, wherein the endoprosthesis comprises a trellis which is formed by at least one resilient filament, the at least one runner being formed by an extension of at least one filament of the trellis.

5. An implant according to claim 2, wherein an edge of the separation surface is articulated to an edge of the outer peripheral surface.

6. An implant according to claim 1, wherein the at least one runner is mounted in a detachable manner on the endoprosthesis.

7. An implant according to claim 6, wherein the at least one runner comprises a rigid tubular support which is pressed on the outer peripheral surface during operation, the spacing member being configured to be deployed radially from the tubular support.

8. An implant according to claim 1, wherein the at least one member is articulated to the separation surface.

9. An implant according to claim 1, wherein the at least one runner has a cross-section, taken in a center plane which extends through the longitudinal axis, substantially in the form of a V.

10. An implant according to claim 9, wherein the endoprosthesis comprises a shutter which is permanently mounted in the inner passage, the shutter having a cross-section, taken in a center plane which extends through the longitudinal axis, which converges in the opposite direction to the V-shaped cross-section of the at least one runner.

11. An implant according to claim 1, wherein the spacer is permeable with respect to liquids.

12. A method for implanting an implant according to claim 1 in a blood vessel comprising a natural valve having leaflets, the method comprising:

moving the implant into the blood vessel in a deployment device, deploying the at least one runner and introducing the leaflets of the natural valve in the confinement housing;

deploying the endoprosthesis to the dilated configuration;

wherein, when the implant is maintained in a state of radial compression in the blood vessel, after deploying the endoprosthesis, the at least one member of the at least one runner is retained with radial spacing from the separation surface and the outer peripheral surface, the maximal radial width of the housing being less than the maximal radial width of the spacer, the spacer having a maximal radial width which is not equal to zero, and wherein the runner maintains the leaflet of the natural valve away from the wall of the blood vessel in the confinement housing.

13. An implant for placement in a blood vessel, the implant comprising:

an endoprosthesis having a longitudinal axis and being configured to be deployed spontaneously in a radial manner from a compressed configuration to a dilated configuration, the endoprosthesis delimiting an inner passage for blood flow and an outer peripheral surface;

at least one runner for radial support and co-operating with the endoprosthesis, the at least one runner comprising a separation surface extending radially with respect to the outer peripheral surface and at least one member being configured to be deployed away from the longitudinal axis relative to the separation surface;

wherein the runner is arranged so as to delimit
a confinement housing which extends between the separation surface and the outer peripheral surface; and
a radial spacer which is formed by the separation surface and the at least one member;

wherein, when the implant is retained in a state of radial compression around the at least one runner, with the endoprosthesis being in the dilated configuration, the maximum radial width of the confinement housing is less than the maximum radial width of the spacer, the spacer having a maximum radial width which is not equal to zero, wherein the confinement housing is configured to receive a leaflet of a natural valve when the implant is implanted in the blood vessel, and wherein the runner is configured to maintain the leaflet of the natural valve away from a wall of the blood vessel in the confinement housing.

14. An implant for placement in a blood vessel, the implant comprising:

an endoprosthesis having a longitudinal axis, and being configured to be deployed spontaneously in a radial manner from a compressed configuration to a dilated configuration, the endoprosthesis delimiting an inner passage for blood flow and an outer peripheral surface;

at least one runner for radial support and co-operating with the endoprosthesis, the at least one runner comprising a separation surface extending radially with respect to the outer peripheral surface and at least one member configured to be deployed away from the longitudinal axis relative to the separation surface;

wherein the runner is arranged so as to delimit
a confinement housing, for receiving a leaflet of natural valve, which extends between the separation surface and the outer peripheral surface; and
a radial spacer which is formed by the separation surface and the at least one member;

wherein, when the implant is retained in a state of radial compression, with a leaflet of natural valve housed into the confinement housing, the maximum radial width of the housing is less than the maximum radial width of the spacer, the spacer having a maximum radial width which is not equal to zero, and wherein the runner is configured to maintain the leaflet of the natural valve away from a wall of the blood vessel in the confinement housing.

* * * * *